United States Patent [19]
Gao et al.

[11] Patent Number: 5,442,118
[45] Date of Patent: Aug. 15, 1995

[54] ASYMMETRIC SYNTHESIS OF (R)- AND (S)-ARYLETHANOLAMINES FROM IMINOKETONES

[75] Inventors: Yun Gao, Southborough; Yaping Hong, Worcester; Charles M. Zepp, Berlin, all of Mass.

[73] Assignee: Sepracor, Inc., Marlborough, Mass.

[21] Appl. No.: 231,231

[22] Filed: Apr. 22, 1994

[51] Int. Cl.[6] .......................... C07C 213/00
[52] U.S. Cl. ................... 564/356; 564/357; 564/361; 564/363; 564/365; 564/415; 564/489
[58] Field of Search ............... 564/356, 357, 361, 363, 564/365, 415, 489

[56] References Cited

U.S. PATENT DOCUMENTS 5,264,585  11/1993  Blacklock et al. ............... 548/405
5,283,359  2/1994  Tann et al. ....................... 560/53

OTHER PUBLICATIONS

Cho et al, J. Chem. Soc., Perkin Trans. I, (1990) pp. 3200–3201.
Mathre et al. "A Practical Process for the Preparation of Tetrahydro-1-methyl-3,3-diphenyl-1 . . . " *J. Org. Chem.* 58, 2880–2888 (1993).
Cho et al."Enantioselective Synthesis of Optically Active β-Aminoalcohols via Asymmetric Reduction" *Tetrahedron: Asymmetry* 3, 341–342 (1992).
Alcaide et al., "Stereochemistry of Imino-group Reduction. Part 6. Stereochemistry of Reduction of 1,2-Imino Ketones . . . " *J. Chem Soc. P. II.*, 99–103 (1986).
Alcaide et al. "Reduction of N-Substituted 1-Acetyl- and 1-Benzoyl-ethanimines" *J.l Chem. Research*, 98–99 (1988).

*Primary Examiner*—Richard L. Raymond
*Attorney, Agent, or Firm*—Heslin & Rothenberg

[57] ABSTRACT

A method for the enantioselective reduction of an α-iminoketone to an α-aminoalcohol is disclosed. The method utilizes a borane reducing agent as the reducing agent and a chiral 1,3,2-oxazaborole as the catalyst. The method is applied to the synthesis of R-albuterol from methyl 5-acetylsalicylate in high yield and high optical purity.

13 Claims, No Drawings

ASYMMETRIC SYNTHESIS OF (R)- AND (S)-ARYLETHANOLAMINES FROM IMINOKETONES

FIELD OF THE INVENTION

The invention relates to a method for the enantiospecific reduction of an α-iminoketone to an αaminoalcohol, particularly an arylethanolamine. The method comprises reacting an α-iminoketone with a borane reducing agent in the presence of a 1,3,2-oxazaborolidine catalyst.

BACKGROUND OF THE INVENTION

2-Amino-1-arylethanol derivatives, such as albuterol (I), terbutaline (II), isoproterenol (III), and sotalol (IV), are well known pharmaceutical agents.

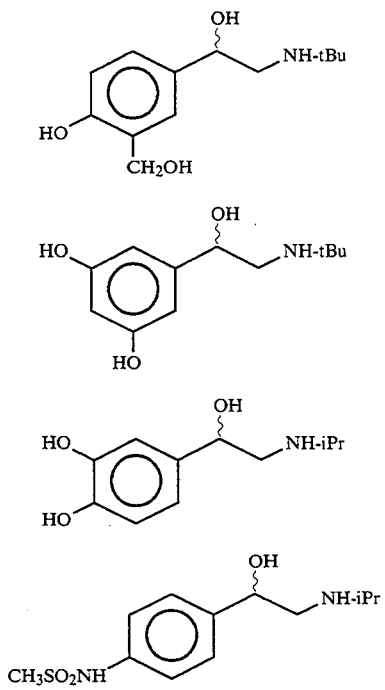

These and other β-adrenergic agents (β-blockers or β-agonists) are used in the treatment of asthma, glaucoma and cardiovascular diseases. As a class, the 2-amino-1-arylethanols possess at least one enantiogenic center. It is often the case that two enantiomers of a chiral drug display different biological activities, and although the enantiomers of many arylethanolamine drugs appear to exhibit this dichotomous activity, to date only a few optically pure arylethanolamine drugs have been prepared. This is probably because the synthetic approaches to arylethanolamines generally involve (1) tedious diastereomeric resolutions, (2) high-cost reagents, or (3) lengthy multistep syntheses with low overall yields. In fact, the only published method for preparation of an optically pure albuterol enantiomer is by the resolution of a benzyl-protected ester precursor [Hartley and Middlemiss, *J. Med. Chem.* 14, 895 (1971)]. A simple synthesis of enantiomerically pure arylethanolamines would be highly desirable.

Initially one might consider the enantiospecific reduction of the ketone functionality in an α-aminoketone, because α-aminoketones are common intermediates in the syntheses of the above-mentioned β-agonists and β-blockers.

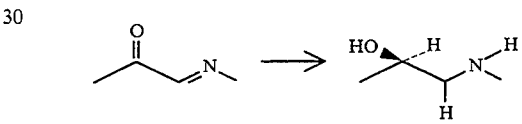

It has been reported that asymmetric hydrogenation of α-amino ketones in the presence of a ruthenium complex gives α-aminoalcohols with high enantioselectivity. However, catalytic hydrogenation is often less attractive than hydride-type reductions in that, with hydrides or borane, additional functionalities (such as the ester in an albuterol precursor) can, in principle, be reduced in the same step as the ketone.

Asymmetric reductions of prochiral ketones with borane in the presence of chiral oxazaborolidine catalysts are known, and high enantioselectivities have been observed with many ketones. Unfortunately, the high enantioselectivity observed with simple ketones has not been achieved in asymmetric borane reduction of α-amino substituted ketones, which give products characterized by disappointingly low enantiomeric excesses (ee).

α-Iminoketones are one step closer to starting material, and the simultaneous reduction of both the ketone and the imine functionalities would eliminate one step in the overall synthesis.

The known racemic mixture of albuterol isomers(I) has, in at least one instance, been prepared by the chirally uncontrolled reduction of an α-iminoketone intermediate (PCT WO 92/04314). There are a few reports on the asymmetric reduction of the C=N functionality with borane, and in the few that have been reported, moderate asymmetric induction has been obtained in some cases [See Cho et al. *J. Chem. Soc. Perkin Trans. I*, 1990, 3200; and Cho et al. *Tetrahedron: Asymmetry*, 3, 337 (1992).] However, no methods appear to have been reported for the asymmetric reduction of α-iminoketones to give α-aminoalcohols.

SUMMARY OF THE INVENTION

It is an object of the present invention to provide a general method for the synthesis of optically pure (R)- and (S)-albuterol and similar ethanolamines via the asymmetric reduction of α-iminoketone precursors.

It is a further object to provide a method that is inexpensive and provides reproducible, high yields.

It is an advantage of the process of the invention that it allows the reduction of additional functionalities, such as esters, in the same step as the asymmetric reduction of the iminoketone.

It is a further advantage of one particular embodiment of the invention that it proceeds from an intermediate in an industrial process for albuterol.

These and other objects features and advantages are provided by the present invention, which in one aspect relates to a process for the enantiospecific reduction of an α-iminoketone to an α-aminoalcohol comprising reacting an α-iminoketone with a borane reducing agent, such as borane-dimethyl sulfide or borane-THF, in the presence of a chiral 1,3,2-oxazaborole catalyst. For convenience, the catalysts of the invention will often be referred to in the text as "oxazaborolidines"; in fact, following strict Chemical Abstracts nomenclature, they would be named as derivatives of pyrrolo-oxazaborole, the "idine" suffix conveying the same oxidation state as the "tetrahydro" substituent nomenclature. A preferred catalyst is tetrahydro-1-methyl-3,3-diphenyl-1H,3H-pyrrolo[1,2-c][1,3,2]oxazaborole (A) or its borane complex:

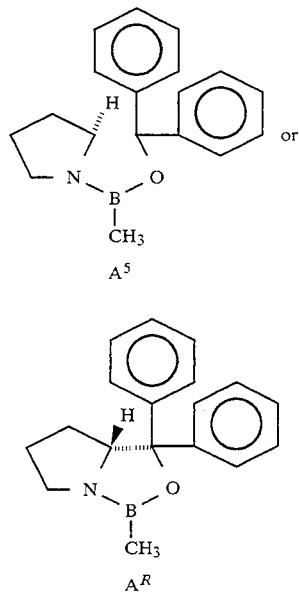

Suitable α-iminoketones include, among others, compounds of formula V

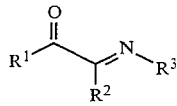

wherein

R¹ is phenyl, substituted phenyl, naphthyl, substituted naphthyl, heteroaryl or substituted heteroaryl;

R² is hydrogen, aryl or lower alkyl; and

R³ is secondary or tertiary alkyl or an aryl group.

In a preferred embodiment R² is hydrogen; in further preferred embodiments R¹ is phenyl or substituted phenyl, R² is hydrogen and R³ is isopropyl or tert-butyl. In a particularly preferred embodiment a precursor to albuterol is reduced to albuterol. The precursor to albuterol can be reduced to predominantly (R)-albuterol in the presence of (R)-tetrahydro-1-methyl-3,3-diphenyl-1H,3H-pyrrolo[1,2-c][1,3,2]oxazaborole.

In one specific aspect the invention relates to a process for producing (S)-albuterol by reacting methyl 5-((1,1-dimethylethyl)imino)acetyl-2-hydroxybenzoate with borane-dimethylsulfide in the presence of (S)-tetrahydro-1-methyl-3,3-diphenyl-1H,3H-pyrrolo[1,2-c][1,3,2]oxazaborole or its borane complex.

In another specific aspect, the invention relates to a process for producing (R)-albuterol comprising reacting methyl 5-((1,1-dimethylethyl)-imino)acetyl-2-hydroxybenzoate with borane-dimethylsulfide in a suitable solvent in the presence of (R)-tetrahydro-1-methyl-3,3-diphenyl-1H,3H-pyrrolo[1,2-c][1,3,2]-oxazaborole.

A preferred solvent is toluene. The reaction is optimally carried out at a temperature between about −20° C. and +20° C., and is carried out either (a) by adding a solution of methyl 5-((1,1-dimethylethyl)imino)-acetyl-2-hydroxybenzoate to a solution of borane-dimethylsulfide and (R)-tetrahydro-1-methyl-3,3-diphenyl-1H,3H-pyrrolo[1,3,2]oxazaborole; or (b) by adding a solution of methyl 5-((1,1-dimethylethyl)imino)acetyl-2-hydroxybenzoate and a solution of borane-dimethylsulfide simultaneously to a solution of (R)-tetrahydro-1-methyl-3,3-diphenyl-1H,3H-pyrrolo[1,2-c][1,3,2]oxazaborole.

Detailed Description Inclusive of Preferred Embodiments

The general synthesis of arylethanolamines of the invention is shown in scheme A. The method is particularly simple and practical because it proceeds via readily available α-iminoketones (Va):

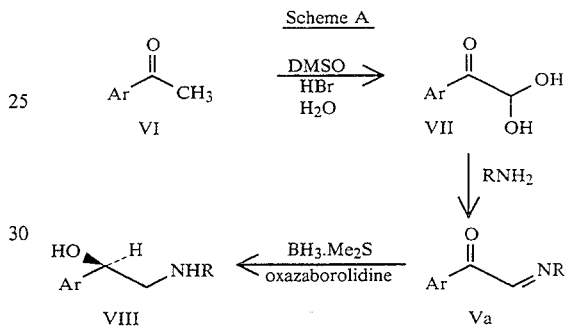

The graphic representations of racemic, ambiscalemic and scalemic or enantiomerically pure compounds used herein are taken from Maehr *J. Chem. Ed.* 62, 114–120 (1985). Thus, solid and broken wedges (as in A) are used to denote the absolute configuration of a chiral element; wedge outlines and dotted or broken lines (e.g. VIII) denote enantiomerically pure compounds of indeterminate absolute configuration. As usual, a wavy line indicates a mixture of enantiomers of indeterminate proportion, commonly a racemic mixture.

The term "enantiomeric excess" is well known in the art and is defined for a resolution of ab→a+b as $$ee_a = \left( \frac{\text{conc. of } a - \text{conc. of } b}{\text{conc. of } a + \text{conc. of } b} \right) \times 100$$

The term "enantiomeric excess" is related to the older term "optical purity" in that both are measures of the same phenomenon. The value of ee will be a number from 0 to 100, zero being racemic and 100 being pure, single enantiomer. A compound which in the past might have been called 98% optically pure is now more precisely described as 96% ee. Processes that yield products of ee less than about 80% are not generally regarded as commercially attractive. Processes that yield albuterol of ee greater than about 96% are particularly attractive because the eutectic of albuterol is about 96–97%, and thus substantially pure single enantiomers can be obtained by simple recrystallization of the product.

Arylglyoxals (VII) are most conveniently prepared from acetophenone derivatives by the procedure of PCT application 92/04314, although other syntheses, well known to persons of skill in the art, are also suitable.

In the case of albuterol, the starting material, methyl 5-acetylsalicylate (VIa), is commercially available. Oxidation in DMSO (1.0M) in the presence of 2 equivalents of aqueous HBr proceeds smoothly at 60° C. over 20 hours in greater than 80% yield to give the arylglyoxal (VIIa) as a yellow solid. Without further purification, this compound is treated with 1.0–1.2 eq of t-BuNH$_2$ in warm toluene or ethyl acetate to give the iminoketone (Vb) in greater than 0% yield. The iminoketone can be purified by recrystallization from toluene/heptane and is used in the reduction after drying. Overall yield from the salicylate is greater than 60%.

The complete synthesis is outlined in Scheme B.

tetrahydro-1-methyl-3,3-diphenyl-1H,3H-pyrrolo[1,2-c][1,3,2]-oxazaborole (A) or its borane complex;

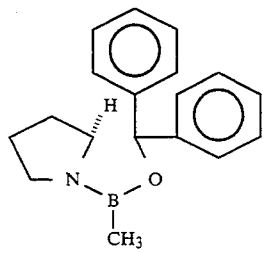

catalyst B was 4,5-diphenyl[1,3,2]oxazaborolidine; catalyst C was 4,5-diphenyl-2-methyl-[1,3,2]-oxazaboroli-

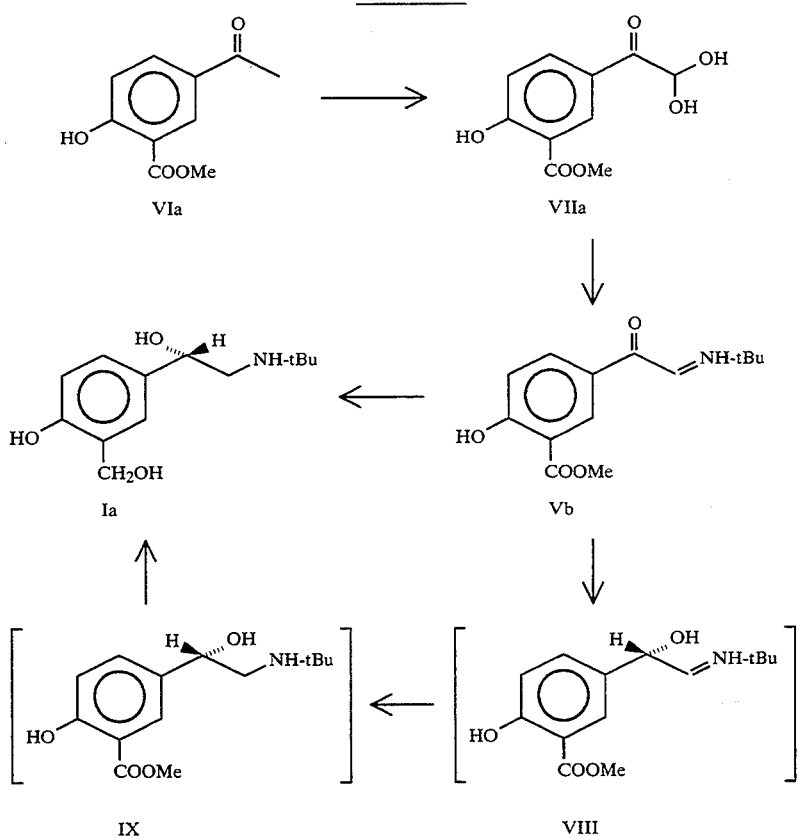

The reduction with three equivalents of borane is depicted as proceeding through the intermediate imine-alcohol-ester VIII and aminoalcohol-ester IX to the aminodiol Ia, but the intermediates have not been isolated or identified; the sequence is presented for heuristic purposes only.

The advantages of this route are: (a) it follows an industrial process for racemic albuterol that has been developed for the production of racemic albuterol in multi kilo quantities; (b) it is short (only three steps); and (c) it represents a new general method applicable to the synthesis of related optically active arylethanolamine derivatives such as salmeterol, etilefrine, isoproterenol, terbutaline, etc.

The optimal catalyst for a particular substrate is a matter of experimentation. For albuterol five catalysts were examined: catalyst A, the catalyst of choice, was dine; catalyst D was 3,3a,8,a-tetrahydro-2H-indeno[1,2-d][1,3,2]oxazaborole; and catalyst E was 5,5-diphenyl-4-[2-(methylthio)ethyl][1,3,2]-oxazaborolidine. Catalyst A was prepared according to the method of Mathre et al. [*J. Org. Chem.* 58, 2880–2888 (1993)]; catalysts B and C were prepared by the method of Quallich and Woodall [Syn. Lett. 1993,929]; catalyst D was prepared in situ from (1S,2R)-cis-1-amino-2-indanol; and catalyst E was prepared in situ according to the procedure of Mehler and Martens [*Tetrahedron: Asymmetry* 4, 1983 and 2299 (1993)].

The above catalysts were tested in the reduction of the iminoketone precursor Vb under similar conditions (some variations based on further experiments, vide infra). The best result was obtained with catalyst A. The absolute configuration of albuterol product was determined by HPLC using a reference standard. It was found that in the case of albuterol, the S-enantiomer predominated when using S-catalysts derived from natural L-amino acids (e.g. L-proline). Thus, in order to prepare (R)-albuterol, the preferred R-catalyst ($A^R$)

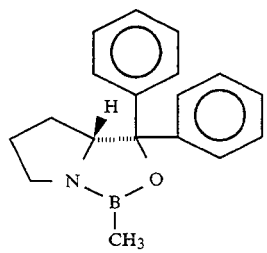

$A^R$ has to be prepared from D-proline. The results are summarized in Table 1. Based on these results, catalyst A was used in subsequent studies.

TABLE 1

Nature of the catalysts in reduction of ketoimine (3)[a]

| Entry | Condition | Catalyst (mol %) | ee (%)[b] | Conversion (%) |
|---|---|---|---|---|
| 1 | toluene, rt, slow addition | A (20%) | 76 (S) | >99 |
| 2 | CH$_2$Cl$_2$ −20% C., slow addition | B (20%) | 6 (S)[c] | 99 |
| 3 | toluene, rt, slow addition | C (100%) | 33 (S) | 89 |
| 4 | toluene, rt, slow addition | D (100%) | 70 (S) | 99 |
| 5 | CH$_2$Cl$_2$, rt, slow addition | E (20%) | 25 (S) | 100 |

[a]Reactions were performed under the standard conditions (see Experimental section) except as noted.
[b]ee were determined by HPLC on a Sumichiral OA 4900 column or equivalent.
[c]Low ee may have been due to impure catalyst.

It is often observed in asymmetric catalysis that the order and conditions of addition of reagents and substrate significantly affect the degree of asymmetric induction. Although no detailed study of this effect appears in the literature for the asymmetric reduction of ketones with borane in the presence of the oxazaborolidine catalyst, the reduction is usually performed by adding the substrate last in the chosen solvent. Initially, the reduction of iminoketone with borane was performed in this manner by mixing all components together. However, as shown in Table 2, the ee of albuterol obtained was disappointingly low (entry 1).

By slow addition of the iminoketone over a period of 3 hours to the solution of borane and the catalyst, the enantioselectivity increased dramatically (entries 2 and 4). The enhanced enantioselectivity may be due to the fact that under these conditions, the effective concentration of the catalyst is higher. It may also be that the keto group is reduced faster than the imine group, and the resulting intermediate imine-alcohol (VIII) does not complex with borane as strongly as the catalyst does to affect the asymmetric induction. When the iminoketone and borane were added simultaneously to the catalyst solution over a period of 3 hours, slightly higher ee's were obtained (entries 3 and 5).

TABLE 2

| Entry | Addition manner and condition (20 mol % A) | ee (%) | Conversion (%) |
|---|---|---|---|
| 1 | CH$_2$Cl$_2$, −20° C., all together | 5–35 | 85–100 |
| 2 | CH$_2$Cl$_2$, −20° C., sm added slowly (3 h) | 83 | >99 |
| 3 | toluene, −20° C., sm and BH$_3$ added slowly (3 h) | 83 | >99 |
| 4 | toluene, 20° C., sm added slowly (3 h) | 76 | >99 |
| 5 | toluene, 20° C., sm and BH$_3$ added slowly (3 h) | 85 | >99 |

Two solvents, toluene and methylene dichloride, were examined. The literature indicates that higher ee are obtained in the reduction of simple ketones in CH$_2$Cl$_2$ than in toluene. In the present invention, toluene gives higher ee in the reduction of the iminoketone with 20 mol% catalyst A, as shown in Table 3. This is an unexpected advantage, since toluene is much preferred over CH$_2$Cl$_2$ for industrial processes.

TABLE 3

Effects of solvent

| Entry | Solvent | Conditions | ee (%) | Conversion (%) |
|---|---|---|---|---|
| 1 | CH$_2$Cl$_2$ | −20° C., sm added slowly | 83 | >99 |
| 2 | Toluene | −20° C., sm added slowly | 87 | 99 |

Both stereoselectivity and chemoselectivity commonly depend on the reaction temperature. This effect was examined in more detail using 20 mol% catalyst A by slow addition of the iminoketone over 3 to 4 hours. The results are presented in Table 4. At −40° C. or below, the reaction was slow, and after warming up to normal temperature, low ee product was obtained due to presence of excess of starting material. At −20° C. good selectivity was observed. Little difference in selectivity was observed between reactions at 0° C. and at −20° C.; 0° appears to be a convenient temperature.

TABLE 4

Effects of temperature

| Entry | Solvent | Temperature (°C.) | ee (%) | Conversion (%) |
|---|---|---|---|---|
| 1 | CH$_2$Cl$_2$ | −40 | 36 | 88 |
| 2 | CH$_2$Cl$_2$ | −20 | 83 | >99 |
| 3 | CH$_2$Cl$_2$ | 0 | 83 | 94 |
| 4 | toluene | −20 | 87 | 99 |
| 5 | toluene | −20 | 86 | >99 |
| 6 | toluene | 20 (10 mol % A) | 76 | 99 |
| 7 | toluene | 20 (simultan. add.) | 85 | 100 |

It is desirable to minimize the amount of catalyst used in the reduction. To obtain the ceiling ee in this reduction, a reaction with 100 mol% catalyst A was performed and albuterol of 97% ee was obtained. As shown in Table 5, when the reaction was performed by simultaneous addition of the iminoketone and borane to the catalyst solution in toluene at 0° C., ee's in the range of 93–95% could still be obtained with only 10 mol% catalyst. This is an industrially practical range for the preparation of optically pure albuterol.

TABLE 5

| Entry | Conditions | mol % of A | ee (%) | Conversion (%) |
|---|---|---|---|---|
| 1 | CH$_2$Cl$_2$, sm added slowly (3 h), −20° C. | 20 | 83 | >99 |
| 2 | CH$_2$Cl$_2$, sm added slowly (3 h), −20° C. | 100 | 97 | 85 |
| 3 | same as above, 5 h addition | 10 | 44.2 | >99 |
| 4 | CH$_2$Cl$_2$, simultan. add over 5 h | 10 | 72.7 | 96 |
| 5 | toluene, 0° C., sm added slowly (3 h) | 50 | 95.5 | 100 |
| 6 | toluene, 0° C., simultan. addition | 30 | 96 | >99 |
| 7 | toluene, same as above | 10 | 93 | >99 |
| 8 | toluene, same as above | 10 | 95 | >99 |

The extension of the method to other chiral arylethanolamines such as salmeterol, etilefrine, isoproterenol, terbutaline, Beecham's BRL 35,135 and BRL37,344 and Lederle's CL 316,243, is illustrated by the asymmetric reductions of the model iminoketones Vc, Vd and Ve:

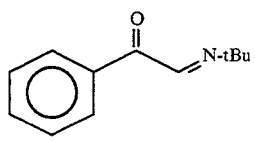 Vc

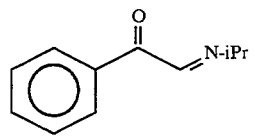 Vd

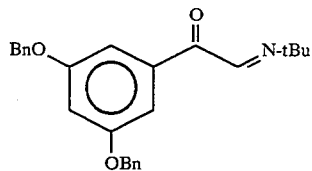 Ve

The ketoimines were prepared by reaction of the corresponding arylglyoxal with branched primary amines such as t-butylamine and isopropylamine. An attempt to isolate the ketoimine from the reaction of an arylglyoxal with a straight chain primary amine failed, perhaps because of the instability of the product ketoimine (polymerization and hydrolysis). However, it is believed that the process will be effective with any imine (straight chain or otherwise) that can be obtained in pure form. Iminoketone Vc is a model compound for albuterol. Iminoketone Vd is a model compound for BRL35,135, BRL 37,344, CL 316,243, isoproterenol, metaproterenol, sotalol and labetalol. Iminoketone Ve is a precursor for terbutaline. (It leads to terbutaline after debenzylation with H$_2$ Pd/C). The results of asymmetric reductions of iminoketones Vc-Ve are summarized in Table 6.

TABLE 6

| | | Variation of substrates* | | |
|---|---|---|---|---|
| Entry | Substrate | mol % A | ee (%) | Yield (%)[b] |
| 1 | Vc | 20 | 85 | 99 |
| 2 | Vd | 20 | 93 | 71 |
| 3 | Ve | 20 | (85–90)[c] | 90 |

[a]Reactions were performed in toluene at 0 C. by simultaneous addition of ketoimine and borane to the catalyst solution.
[b]Yields are isolated yields.
[c]Estimated value, HPLC method is not available.

Thus, a new practical and general method for the preparation of optically active (S)- and (R)-albuterol and other arylethanolamines has been developed. This method represents the preferred process for the synthesis of these compounds because the process consists of only three steps and the asymmetric induction is catalytic in nature. Catalyst A or its borane complex appears to be best for albuterol. Albuterol of 93–95% ee can be obtained with 10 mol% catalyst under the optimized conditions. Good results are obtained using toluene as solvent, thus making the process more industrially practical.

EXAMPLES

The synthesis of arylglyoxal (VIIa) follows a modified literature procedure (Floyd, M. B., et al. *J. Org. Chem.* 50, 5022 (1985)) and is described here for methyl 5-acetylsalicylate (VIa).

A 500 mL three neck flask was charged with 150 mL of DMSO and methyl 5-acetylsalicylate (39 g, 0.2 mol). Aqueous HBr (48%, 46 mL, 0.4 mol, 2.0 eq) was added dropwise over 30 min. After addition, the solution was heated at about 60° C. for about 20 hours (followed by TLC or HPLC) until the disappearance of starting material. The yellow mixture was poured onto 400 g of ice with stirring. After stirring for 30 min, the yellow solid was collected by filtration and washed with 2×50 mL of cold water and toluene to give the arylglyoxal (VIIa) (crude yield ca. 80% based on dried material). The wet solid was dried at room temperature under vacuum for 4 hours and used in the next step without further purification.

Reaction of arylglyoxal (VIIa) with t-butylamine to give iminoketone (Vb) was performed in toluene or ethyl acetate as follows:

The wet solid from above (1.0 eq, based on 0.2 mol, 100% yield) and 1.1 eq of t-butylamine (0.22 mol, 23 mL) were dissolved in 200 mL of toluene. The solution was heated at about 40° C. for about 2 hours. The solution was then cooled to room temperature and washed with brine (2×50 mL) and concentrated to dryness under vacuum to give crude iminoketone (Vb) as a yellow solid (33.4 g, 63% yield from methyl 5-acetylsalicylate). The crude iminoketone can be further purified by recrystallization from toluene/heptane to give pure iminoketone (Vb).

The reduction of iminoketone (Vb) with 10 mol% of catalyst A was as follows:

A 25 mL three neck flask equipped with a refluxing condenser and a thermometer was charged with 2 mL of anhydrous toluene and 0.1 mmol of catalyst A[s] (10 mol%) at room temperature under nitrogen. After cooling to 0° C., 300 μl of BH$_3$Me$_2$S (BMS) (10M, 2.0 mmol, 3.0 eq) and a solution of 1 mmol of ketoimine (Vb) (1.0 eq) in 3 mL of toluene were added simultaneously via syringe over 3 hours at 0° C. After addition, the solution was stirred for an additional hour, then was heated to reflux for 5 hours. After cooling to 5° C., the reaction mixture was quenched with 2 mL of methanol. The resulting solution was stirred at room temperature for 10 minutes and then at reflux for 3 hours. The solvent and methanol were removed by distillation. The residual white solid was washed with 3×6 mL of 2:1 hexane/ethyl acetate at 50°-60° C. The solid was further purified by passing through a short pad of silica gel (0.5 cm) eluting with methanol. After removal of methanol, optically active (S)-albuterol was obtained in >90% yield; the ee was found by HPLC to be 93-95% (Sumichiral OA 4900 column. Mobile phase: hexane/$CH_2Cl_2$/MeOH/$CF_3CO_2H$(240:140:20:1); Flow rate: 1 mL/min; Detector: UV 280 nm; Injection volume: 20 μl of 1 mg/mL sample).

While the invention has been particularly shown and described with reference to preferred embodiments thereof, it will be understood by those skilled in the art that other changes in form and details may be made therein without departing from the spirit and scope of the invention.

We claim:

1. A process for the enantiospecific reduction of an α-iminoketone to an α-aminoalcohol comprising reacting an α-iminoketone with a borane-reducing agent in the presence of a chiral 1,3,2-oxazaborole catalyst.

2. A process according to claim 1 wherein said 1,3,2-oxazaborole catalyst is (R) tetrahydro-1-methyl-3,3-diphenyl-1H,3H-pyrrolo[1,2-c][1,3,2]oxazaborole or its borane complex:

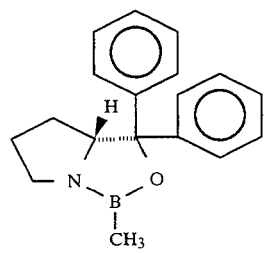

3. A process according to claim 1 wherein said 1,3,2-oxazaborole catalyst is (S) tetrahydro-1-methyl-3,3-diphenyl-1H,3H-pyrrolo[1,2-c][1,3,2]oxazaborole or its borane complex:

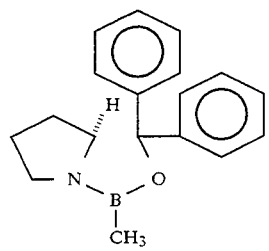

4. A process according to claim 1 wherein said α-iminoketone is of the formula

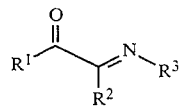

wherein
$R^1$ is phenyl, substituted phenyl, naphthyl substituted naphthyl, heteroaryl or substituted heteroaryl;
$R^2$ is hydrogen, aryl or alkyl; and
$R^3$ is secondary or tertiary alkyl or an aryl group.

5. A process according to claim 4 wherein $R^1$ is phenyl or substituted phenyl; $R^2$ is hydrogen; and $R^3$ is isopropyl or tert-butyl.

6. A process according to claim 5 wherein a precursor to albuterol is reduced to albuterol.

7. A process according to claim 6 wherein a precursor to albuterol is reduced to predominantly (R)-albuterol in the presence of (R)-tetrahydro-1-methyl-3,3-diphenyl-1H,3H-pyrrolo[1,2-c][1,3,2]oxazaborole.

8. A process for producing (S)-albuterol comprising reacting methyl 5-((1,1-dimethylethyl)imino)acetyl-2-hydroxybenzoate with borane-dimethylsulfide in the presence of (S)-tetrahydro-1-methyl-3,3-diphenyl-1H,3H-pyrrolo[1,2-c][1,3,2]oxazaborole.

9. A process for producing (R)-albuterol comprising reacting methyl 5-((1,1-dimethylethyl)imino)acetyl-2-hydroxybenzoate with borane-dimethylsulfide in a suitable solvent in the presence of (R)-tetrahydro-1-methyl-3,3-diphenyl-1H,3H-pyrrolo[1,2-c][1,3,2]oxazaborole.

10. A process according to claim 9 wherein said solvent is toluene.

11. A process according to claim 9 wherein said reaction is carried out at a temperature between about −20° C. and +20° C.

12. A process according to claim 9 wherein said reaction is carried out by adding a solution of methyl 5-((1,1-dimethylethyl)imino)acetyl-2-hydroxybenzoate to a solution of borane-dimethylsulfide and (R)-tetrahydro-1-methyl-3,3-diphenyl-1H,3H-pyrrolo[1,2-c][1,3,2]oxazaborole.

13. A process according to claim 9 wherein said reaction is carried out by adding a solution of methyl 5-((1,1-dimethylethyl)imino)acetyl-2-hydroxybenzoate and a solution of borane-dimethylsulfide simultaneously to a solution of (R)-tetrahydro-1-methyl-3,3-diphenyl-1H,3H-pyrrolo[1,2-c][1,3,2]oxazaborole.

* * * * *

UNITED STATES PATENT AND TRADEMARK OFFICE
CERTIFICATE OF CORRECTION

PATENT NO. : 5,442,118
DATED : Aug. 15, 1995
INVENTOR(S) : Gao et al.

It is certified that error appears in the above-indentified patent and that said Letters Patent is hereby corrected as shown below:

Column 12:

Claim 13, delete the following structure:

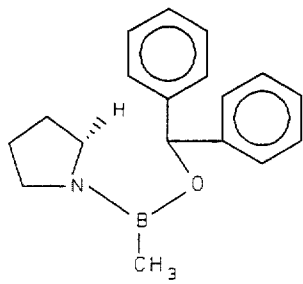

UNITED STATES PATENT AND TRADEMARK OFFICE
CERTIFICATE OF CORRECTION

PATENT NO.   : 5,442,118
DATED        : August 15, 1995
INVENTOR(S)  : Yun Gao, et al.

It is certified that error appears in the above-indentified patent and that said Letters Patent is hereby corrected as shown below:

and insert therefor

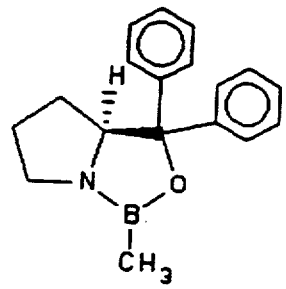

Signed and Sealed this

Twenty-sixth Day of December, 1995

Attest:

BRUCE LEHMAN

*Attesting Officer*    Commissioner of Patents and Trademarks